United States Patent [19]

Bornzin et al.

[11] Patent Number: 5,476,483
[45] Date of Patent: Dec. 19, 1995

[54] SYSTEM AND METHOD FOR MODULATING THE BASE RATE DURING SLEEP FOR A RATE-RESPONSIVE CARDIAC PACEMAKER

[75] Inventors: Gene A. Bornzin, Camarillo; Elia R. Arambula, Artesia; Joseph J. Florio, Sunland, all of Calif.

[73] Assignee: Pacesetter, Inc., Sylmar, Calif.

[21] Appl. No.: 258,292

[22] Filed: Jun. 10, 1994

[51] Int. Cl.$^6$ .................................................. A61N 1/365
[52] U.S. Cl. ............................................................... 607/17
[58] Field of Search ............................................... 607/77

[56] References Cited

U.S. PATENT DOCUMENTS

| 5,040,534 | 8/1991 | Mann et al. | 128/419 PG |
| 5,074,302 | 12/1991 | Poore et al. | 128/419 PG |
| 5,143,065 | 9/1992 | Adkins et al. | 128/419 PG |

OTHER PUBLICATIONS

Michael T. Lee and Ross Baker, "Circadian Rate Variation in Rate Adaptive Pacing Systems," Page, vol. 13, pp. 1797 1801, Dec. 1990.

Milan Djordjevic, rt al., "Circadian Variations of Heart and Stim-T Interval: Adaptation for Nighttime Pacing," Pace, vol. 12, pp. 1757–1762, Nov. 1989.

*Primary Examiner*—William E. Kamm
*Attorney, Agent, or Firm*—Lisa P. Weinberg

[57] ABSTRACT

A system and method are provided for modulating the base rate of a transfer function for a rate-responsive cardiac pacemaker. Activity sensor measurements are used to derive activity variance measurements, which in turn are used to modulate the base pacing rate. In one embodiment, a histogram is used to store activity variance measurements collected over a period of about a week. The histogram is used to derive an activity variance threshold, which is compared to current activity variance measurements to determine if the patient is sleeping. If the patient is deemed to be sleeping, the pacing rate is set to a rate that comfortably meets the patient's low metabolic demands during sleep. In alternative embodiments, the activity variance measurements are applied to a base rate slope to modulate the base pacing rate.

40 Claims, 7 Drawing Sheets

SYSTEM AND METHOD FOR MODULATING THE BASE RATE DURING SLEEP FOR A RATE-RESPONSIVE CARDIAC PACEMAKER

BACKGROUND OF THE INVENTION

This invention relates to implantable cardiac pacemakers, and particularly to rate-responsive cardiac pacemakers. More particularly, this invention relates to a system and method for modulating the base rate by a transfer function for a rate-responsive pacemaker, between a resting rate that is suitable for the patient while awake but at rest, and a sleeping rate that meets the patient's low metabolic demands during sleep.

A pacemaker is an implantable medical device that delivers electrical stimulation pulses to cardiac tissue to relieve symptoms associated with bradycardia—a condition in which a patient cannot normally maintain a physiologically acceptable heart rate. Early pacemakers delivered stimulation pulses at regular intervals in order to maintain a predetermined heart rate—typically a rate deemed to be appropriate for the patient at rest. The predetermined rate was usually set at the time the pacemaker was implanted, although in more advanced pacemakers, the rate could be set remotely after implantation. Such pacemakers were known as "asynchronous" pacemakers because they did not synchronize pacing pulses with natural cardiac activity.

Early advances in pacemaker technology included the ability to sense the patient's natural cardiac rhythm (i.e., the patient's intracardiac electrogram, or "IEGM"). This led to the development of "demand pacemakers"—so named because they deliver stimulation pulses only as needed by the heart. Demand pacemakers are capable of detecting a spontaneous, hemodynamically effective cardiac contraction which occurs within a predetermined time period (commonly referred to as the "escape interval") following a preceding contraction. When a naturally occurring contraction is detected within the escape interval, the demand pacemaker does not deliver a pacing pulse. The ability of demand pacemakers to avoid delivery of unnecessary stimulation pulses is desirable because pacing pulse inhibition extends battery life and avoids competition with the patient's intrinsic rhythm.

Modern demand pacemakers allow physicians to telemetrically adjust the length of the escape interval, which has the effect of altering the heart rate maintained by the device. However, in early devices, this flexibility only allowed for adjustments to a fixed programmed rate, and did not accommodate patients who required increased or decreased heart rates to meet changing physiological requirements during periods of elevated or reduced physical activity. Therefore, unlike a person with a properly functioning heart, a patient receiving therapy from an early demand pacemaker was paced at a constant heart rate—regardless of the level to which the patient was engaged in physical activity. Thus, during periods of elevated physical activity, the patient was subject to adverse physiological consequences, including lightheadedness and episodes of fainting, because the heart rate was forced by the pacemaker to remain constant.

The adverse effects of constant rate pacing lead to the development of "rate-responsive pacemakers" which can automatically adjust the patient's heart rate in accordance with metabolic demands. An implanted rate-responsive pacemaker typically operates to maintain a predetermined minimum heart rate when the patient is engaged in physical activity at or below a threshold level, and gradually increases the maintained heart rate in accordance with increases in physical activity until a maximum rate is reached. Rate-responsive pacemakers typically include processing circuitry that correlates measured physical activity to an appropriate heart rate. In many rate-responsive pacemakers, the minimum heart rate, maximum heart rate, and a slope defining transition rates between the minimum heart rate and the maximum heart rate, are parameters that may be telemetrically adjusted to meet the needs of a particular patient.

One approach that has been considered for enabling rate-responsive pacemakers to determine an appropriate heart rate involves the use of a physiological parameter that reflects the patient's level of metabolic need. Physiological parameters that have been considered include central venous blood temperature, blood pH level, QT time interval and respiration rate. However, certain drawbacks (such as slow response time, unpredictable emotionally-induced variations, and wide variability across individuals) render the use of these physiological parameters difficult, and accordingly, they have not been widely used in practice.

Rather, most rate-responsive pacemakers employ sensors that transduce mechanical forces associated with physical activity—the level of physical activity being indicative of the patient's level of metabolic need. These activity sensors generally contain a piezoelectric transducing element which generates a measurable electrical potential when a mechanical stress resulting from physical activity is experienced by the sensor. By analyzing the signal from a piezoelectric activity sensor, a rate-responsive pacemaker can determine how frequently pacing pulses should be applied to the patient's heart.

Piezoelectric elements for activity sensors are commonly formed from piezoelectric crystals, such as quartz or barium titanite. Recently, however, activity sensors have been designed which use thin films of a piezoelectric polymer, such as polyvinylidene fluoride (commonly known by the trademark KYNAR, owned by ATOCHEM North America), rather than the more commonly used piezoelectric crystals. Activity sensors so designed are described in copending, commonly-assigned U.S. patent applications Ser. No. 08/059,698, filed May 10, 1993, now U.S. Pat. No. 5,383,473 entitled "A Rate-Responsive Implantable Stimulation Device Having a Miniature Hybrid-Mountable Accelerometer-Based and Method of Fabrication," and Ser. No. 08/091,850, filed Jul. 14 1993, now U.S. Pat. No. 5,425,750 entitled "Accelerometer-Based Multi-Axis Physical Activity Sensor for a Rate-Responsive Pacemaker and Method of Fabrication," which are hereby incorporated by reference in their entireties.

A variety of signal processing techniques have been used to process the raw sensor signals provided by activity sensors. For example, in one approach, the raw signals are rectified and filtered. Alternatively, the frequency at which the highest peaks in the signals occur can be monitored. Regardless of the particular method used, the result is typically a digital signal that is indicative of the level of sensed activity at a given time. In one preferred approach, the digital signal is produced by repeatedly integrating the raw sensor signals until a predetermined threshold value is reached. Each time the threshold is reached, a digital trigger pulse is generated. A counter is used to count the number of trigger pulses that occur in a fixed period of time (e.g., the number of trigger pulses that occur during an approximately 100 ms period within each heartbeat interval). The count reached at the end of the fixed period of time is provided to processing circuitry in the pacemaker, which processing circuitry typically includes a microprocessor.

The processing circuitry then uses the count signal to produce an activity level measurement that represents the patient's activity level. The appropriate rate at which the patient's heart is to be stimulated (known as the sensor-indicated rate) is determined by applying a transfer function to the activity level measurement. The transfer function defines a sensor-indicated rate for each possible activity level measurement.

An example of a rate-responsive pacemaker in which a transfer function is used to calculate the sensor-indicated rate is described in commonly-assigned U.S. Pat. No. 5,074,302 of Poore et al. ("the '302 patent"), which is hereby incorporated by reference in its entirety. As described therein, when relatively little activity is detected, the activity level measurement is ordinarily below a low activity threshold. When the activity level measurement is below the low activity threshold, the sensor-indicated rate is set to a base pacing rate (e.g., 60 beats per minute (bpm)), as defined by the transfer function. At high levels of measured activity, the activity level measurement may exceed a high activity threshold. When this occurs, the sensor-indicated rate is limited to a maximum pacing rate, so that the patient's heart is not stimulated too rapidly. If the value of the activity level measurement falls between the low and high activity thresholds, the pacemaker applies pacing pulses to the patient's heart in accordance with the rate determined by the transfer function, generally at a rate somewhere between the base pacing rate and the maximum pacing rate.

Typically, for activity level measurements between the low and high thresholds, the transfer function is linear. The slope of the transfer function determines increases (or decreases) in the pacing rate corresponding to a given increase (or decrease) in the activity level measurement. The larger the slope, the more rapidly the pacing rate will increase (or decrease).

The slope of the transfer function in typical rate-responsive pacemakers is telemetrically adjustable by a physician, so that the operation of a pacemaker can be tailored to suit an individual patient's needs. During follow-up visits, the slope may be adjusted by the physician if the patient's condition warrants a change. However, for some patients, more frequent slope adjustments may be desirable. In view of this need, pacemakers have been designed which can automatically adjust the slope of the transfer function. The '302 patent describes one such approach—in which high and low averages of activity sensor readings are used in connection with preprogrammed base and maximum pacing rates to derive an appropriate slope for the transfer function.

Another approach for automatically adjusting the slope of the transfer function is described in commonly-assigned, copending U.S. patent application Ser. No. 08/255,194, filed Jun. 7, 1994, entitled "System and Method for Automatically Determining the Slope of a Transfer Function for a Rate-Responsive Cardiac Pacemaker," which is hereby incorporated by reference in its entirety. The approach described therein uses the patient's activity profile, as represented by an activity level histogram stored in the pacemaker's memory, to adjust the slope of the transfer function. The activity level histogram collects activity level measurements over a predetermined period of time, preferably about a week. Each week, the activity level histogram is evaluated to determine if a slope adjustment is warranted. If an adjustment is deemed to be appropriate, the activity level histogram is used, in connection with preprogrammed base and maximum pacing rates, to define the new slope. The activity level histogram is then cleared so that new data may be collected for the next adjustment cycle. In addition, the pacemaker described in copending U.S. patent application Ser. No. 08/255,194, filed Jun. 7, 1994, advantageously inhibits slope adjustment if it is determined that the patient was bedridden for a significant portion the most recent data collection cycle (i.e., the previous week). Further, the above copending U.S. patent application, Ser. No. 08/255,194, filed Jun. 7, 1994, describes an approach that can be used to determine a slope that accommodates a patient's regular exercise routine.

The advances described in the '302 patent and the above copending application Ser. No. 08/255,194, filed Jun. 7, 1994, have lead to the development of extremely flexible pacemakers that enable bradycardia patients to achieve a level of cardiac performance that closely resembles that of healthy individuals. However, there are certain areas in which flexibility can be improved even further. For example, in most rate-responsive pacemakers, the base pacing rate (which, as described above, defines the minimum heart rate maintained by the pacemaker) is usually set telemetrically by the physician in connection with the implantation procedure and then afterward, as needed, during follow-up visits. The base pacing rate is usually set at a rate that comfortably meets the patient's metabolic needs for when the patient is awake but relatively inactive.

While a healthy individual is awake but relatively inactive, the individual's heart rate is usually maintained at a "resting rate." During sleep, the heart rate of a healthy individual typically drops to a "sleeping rate" that is below the resting rate. In this respect, pacemaker-assisted cardiac performance usually differs from what is ordinarily experienced by healthy individuals. More precisely, the fixed base pacing rate of the pacemaker (which is analogous to a healthy individual's resting rate) prevents the patient from experiencing a sleeping rate, which if available, may be more comfortable for the patient during sleep.

The difference between the sleeping rate and the resting rate for healthy individuals is usually rather small (typically in the range from about 10 bpm to about 20 bpm). However, the inability of some pacemakers to maintain a sleeping rate may cause the patient to have some difficulty falling asleep, and may occasionally lead to a restless night of sleep. In addition, since it is likely that a sleeping pacemaker patient being paced at a resting rate could withstand (and even benefit from) a lower sleeping rate, the pacemaker wastes limited energy reserves by maintaining the unnecessarily high resting rate.

In view of the foregoing, it would be desirable if the base pacing rate of a rate-responsive pacemaker could be modulated between a resting rate that is suitable for the patient while awake but relatively inactive, and a sleeping rate that meets the patient's low metabolic demands during sleep. It would also be desirable if the base pacing rate could gradually transition between a sleeping rate and a resting rate, so that abrupt rate changes as the patient transitions between sleep and wakefulness can be avoided.

SUMMARY OF THE INVENTION

In accordance with the present invention, a system and method are provided for modulating the base pacing rate of a rate-responsive pacemaker between a resting rate that is suitable for the patient while at rest but awake, and a sleeping rate that meets the patient's low metabolic demands during sleep.

In a preferred embodiment, the rate-responsive pacemaker includes a conventional pacemaker circuit that is capable of generating pacing pulses in any of the known pacing modes in accordance with instructions provided by processing circuitry (which preferably includes a microprocessor). Pacing pulses are delivered to the patient's heart through at least one conventional pacing lead, which is also used to sense natural cardiac activity when pacing pulses are not being delivered. By sensing natural cardiac activity, the pacemaker is capable of operating in a demand mode, which advantageously extends battery life.

The processing circuitry regulates the operation of the pacemaker circuit in accordance with control routines and parameters that are stored in a memory. The control routines and parameters may be modified by a physician through the use of an external programmer which communicates with the pacemaker through a telemetry circuit included within the pacemaker. In addition, the telemetry circuit may be used to communicate information from the pacemaker to the external programmer, such information including cardiac activity sensed by the pacing lead.

The rate-responsive pacemaker includes a sensor for measuring metabolic need—preferably an activity sensor that measures the patient's level of physical activity at any given time. Preferably, the activity sensor contains a piezoelectric element that generates a measurable electrical potential when a mechanical stress resulting from physical activity is experienced by the sensor. Suitable activity sensors are described in the above-incorporated U.S. patent applications Ser. Nos. 08/059,698 and 08/091,850, now U.S. Pat. Nos. 5,383,473 and 5,425,750, respectively, although other types of activity sensors may be used.

The processing circuitry determines the appropriate pacing rate by applying the activity level measurements to a transfer function. The transfer function may be generally characterized by a base pacing rate for low activity levels, a maximum pacing rate for high activity levels, and a slope that defines pacing rates between the base pacing rate and the maximum pacing rate.

When an activity level measurement is below a low activity threshold, the pacemaker circuit is instructed by the processing circuitry to generate pacing pulses at the base pacing rate as needed by the patient's heart. When an activity level measurement exceeds a high activity threshold, the pacemaker circuit is instructed to generate pacing pulses at the maximum pacing rate, as needed.

The rate at which the rate-responsive pacemaker applies pacing pulses to the patient's heart preferably varies linearly in the region between the base pacing rate and the maximum pacing rate, and is therefore characterized by a slope. (Although a linear relationship between the base pacing rate and the maximum pacing rate is preferred, other relationships may also be used without departing from the spirit of the invention.) The slope of the transfer function allows the pacemaker to deliver pacing pulses at a variable rate in accordance with variations in the activity level measurements. If the pacemaker is operating in accordance with a transfer function that has a gradual slope, changes in the pacing rate will accordingly be more gradual than if the slope were steeper.

Preferably, the maximum pacing rate is telemetrically programmed by the physician. The slope (or other relationship) defining pacing rates between the base pacing rate and the maximum pacing rate may also be programmed by the physician. Alternatively, the slope may be initially programmed by the physician and then automatically adjusted thereafter, as described in the above-incorporated U.S. patent application Ser. No. 08/255,194, filed Jun. 7, 1994.

The base pacing rate may also be telemetrically programmed by the physician and, as described above, it is typically set at a resting rate (e.g., 65 bpm) that is appropriate for when the patient is awake but relatively inactive. However, in accordance with the principles of the present invention, the base pacing rate is not necessarily fixed at the resting rate. Rather, the base pacing rate is modulated between the resting rate and a sleeping rate that is lower than the resting rate. The sleeping rate is preferably set by the physician to a rate that comfortably meets the patient's low metabolic demands during sleep (e.g., 55 bpm).

The present invention provides three approaches for modulating the base pacing rate. In the first approach, the processing circuitry uses information derived from the activity level measurements to determine when the patient falls asleep. After the patient falls asleep, the processor switches the heart rate maintained by the pacemaker from the preprogrammed resting rate to the preprogrammed sleeping rate. While the pacemaker is maintaining the patient's heart rate at the sleeping rate, the processing circuitry continues to monitor the information derived from the activity level measurements to determine when the patient awakens. When the processing circuitry determines that the patient is no longer sleeping, it switches the pacing rate back to the resting rate.

The processing circuitry performs a two part test to determine whether the patient is sleeping. First, the processing circuitry determines if the current activity level measurement is below a low activity threshold. The low activity threshold may be preprogrammed by the physician, but preferably, the low activity threshold is defined by maintaining a running average of the activity level measurements. Since the typical patient is relatively inactive most of the time, the running average approximately corresponds to the patient's resting activity level.

Second, the processing circuitry derives an activity variance measurement from the activity level measurements, and determines if the derived activity variance measurement is below an activity variance threshold. Although the activity variance threshold can also be preprogrammed by the physician, the processor preferably uses an activity variance histogram stored in the pacemaker's memory, along with a preprogrammed parameter that defines the number of hours the patient typically sleeps each day, to determine the activity variance threshold on a periodic basis. The processor uses the preprogrammed number of daily sleep hours to estimate the highest bin of the activity variance histogram that contains activity variance measurements that were derived during sleep. The selected bin defines the activity variance threshold. Preferably, the activity variance histogram contains activity variance measurements collected over a period of about a week.

If the current activity level measurement and the current activity variance measurement are below their respective thresholds, the patient is deemed to be sleeping, and accordingly, the processing circuitry sets the pacing rate to the sleeping rate. Otherwise, the processing circuitry selects a pacing rate in accordance with either the resting rate, the currently active slope of the transfer function, or the maximum pacing rate.

In the second approach for modulating the base pacing rate, the processing circuitry uses a three-term transfer relation that essentially defines the transfer function of the pacemaker (except for the maximum pacing rate, which is programmable). The transfer relation receives as input a sleeping rate, a base rate slope, an activity variance measurement, an activity slope, and an activity level measurement— and provides a heart rate as an output.

A first term of the transfer relation defines the sleeping rate which, as described above, is set to a rate that comfortably meets the patient's metabolic demands during sleep.

The second term is the product of the activity variance measurement (derived by the processor from the activity level measurements) and the base rate slope (which is preprogrammed by the physician). The purpose of the second term is to gradually increase the base pacing rate to rates above the sleeping rate defined by the first term. The base rate slope is preferably set at a rather low level— such that the second term typically contributes only about 0–15 bpm to the base pacing rate. Thus, in accordance with this approach, the base pacing rate is modulated in accordance with the sum of the first and second terms. Like the first approach, activity variance measurements are used to modulate the base pacing rate.

The third term is the product of the activity level measurement and the activity slope (which may be programmed by the physician or automatically selected by the processing circuitry). The third term increases the heart rate defined by the transfer relation from the base pacing rate (as defined by the sum of the first and second terms) to a rate appropriate for the patient's current level of activity.

The main advantage offered by the second approach is that the base pacing rate gradually transitions from the sleeping rate to rates that are appropriate when the patient is awake but relatively inactive. Also, this approach allows the base pacing rate to be set to rates between the sleeping rate and a resting rate, which may be appropriate if the patient is extremely inactive while awake (e.g., bedridden). Another advantage is that there is no need to maintain an activity variance histogram, thereby conserving limited memory space. Although the second approach does not use a fixed resting rate, for practical purposes, the gradual base rate slope effectively limits the base pacing rate to a rate appropriate for when the patient is awake but relatively inactive.

The third approach to modulating the base pacing rate is similar to the second approach, in that a three-term transfer relation defines the transfer function of the pacemaker. The first two terms of the transfer relation define the base pacing rate in substantially the same manner as that described for the second approach. However, in this approach, the third term uses activity variance measurements, instead of activity level measurements, to determine the amount by which the base pacing rate should be increased to accommodate heightened levels of activity.

The activity variance measurements used for the third term are digitally filtered using a relatively short time constant (e.g., about 1.6 minutes). In contrast, the activity variance measurements used for the second term are digitally filtered using a relatively long time constant (e.g., about 38 minutes). The longer time constant results in a filtered activity variance measurement that is resistant to short-term fluctuations in the patient's activity level. This, in turn, causes the first and second terms of the transfer relation to yield a stable base pacing rate that gradually transitions between the sleeping rate and a resting rate. The shorter time constant used to derive the activity variance measurements for the third term allows the transfer relation to respond rapidly when the patient engages in physical activity.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Figure 1:
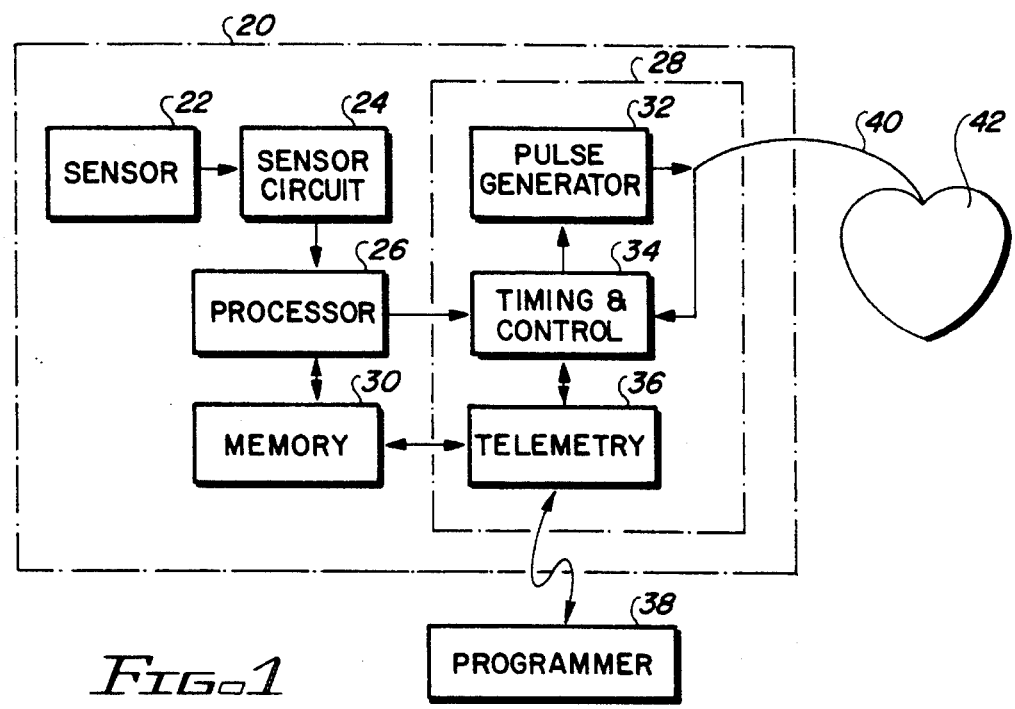
FIG. 1 is a block diagram of a rate-responsive pacemaker which can modulate the base pacing rate of a transfer function in accordance with the principles of the present invention.

Referring first to FIG. 1, a block diagram representing a rate-responsive pacemaker 20 configured in accordance with the principles of the present invention is described. In many respects, the pacemaker 20 operates in a conventional manner to provide pacing pulses at a rate that comfortably meets the patient's metabolic demands. More precisely, the pacemaker 20 uses signals generated by a piezoelectric physical activity sensor 22 to determine the extent to which the patient is engaged in physical activity—the measured level of activity being indicative of metabolic need.

Any sensor that provides a suitable response to physical activity may be used as the sensor 22, including the activity sensors described in the above-incorporated U.S. patent applications Ser. Nos. 08/091,850 and 08/059,698, now U.S. Pat. Nos. 5,425,750 and 5,383,473, respectively. The principles of the present invention may also be applied to pacemakers which use other physiologic sensors to measure metabolic demand, such as blood oxygen sensors, pH sensors, temperature sensors, etc.

The signals generated by the sensor 22 are initially received by a sensor circuit 24. The sensor circuit 24 initially processes the raw signals generated by the sensor 22 to provide digital sensor signals to a processor 26 (which preferably includes a microprocessor (not shown)). In a preferred embodiment, the sensor circuit 24 repeatedly integrates the raw sensor signals from the sensor 22 until a predetermined threshold is reached. Each time the threshold is reached, a digital trigger pulse is generated that increments a counter (not shown) of the sensor circuit 24.

The processor 26 determines the patient's level of activity by periodically examining the contents of the counter of the sensor circuit 24. Preferably, the processor 26 examines the contents of the counter once each heartbeat interval. To conserve power, the sensor circuit 24 is preferably powered for only a small fraction of each heartbeat interval. For example, the sensor circuit 24 may be powered for approximately 100 ms during each heartbeat interval. At the end of the 100 ms period, the processor 26 reads the contents of the counter and then resets the counter for the next heartbeat interval. The processor 26 uses the values read from the counter to derive activity level measurements, in a manner described in greater detail below. Preferably, the sensor 22 and the sensor circuit 24 are calibrated such that about 416 counts corresponds to about one unit of gravity (G) measured by the sensor 22.

In addition to the sensor 22, the sensor circuit 24, and the processor 26, the pacemaker 20 includes a pacemaker circuit 28 (which may be conventional), and a memory 30 coupled to the processor 26. The pacemaker circuit 28 includes a pulse generator circuit 32, a timing and control circuit 34 coupled to the pulse generator circuit 22 and to the processor 26, and a telemetry circuit 36. The telemetry circuit 36, which telemetrically communicates with an external programmer 38, is coupled within the pacemaker 20 to the memory 30 and the timing and control circuit 34.

Coupled to the pulse generator circuit 32 is at least one conventional pacing lead 40 (although more pacing leads can be used if needed, as would be the case for a patient receiving dual-chamber pacing therapy). The pacing lead 40 is used to deliver pacing pulses provided by the pulse generator circuit 32 to the patient's heart 42. In addition, the pacing lead 40 senses the natural rhythm of the heart 42 (e.g., the patient's IEGM), and presents a signal indicative thereof to the timing and control circuit 34. The ability to sense the natural rhythm of the heart 42 enables the pacemaker 20 to operate in a demand mode, in which delivery of a pacing pulse is inhibited by the timing and control circuit 34 when a naturally occurring cardiac contraction is sensed during the escape interval following a preceding contraction.

Although the following description assumes that the pacemaker 20 operates in a demand mode, it should be understood that a simpler implementation is possible, in which the pacemaker 20 does not inhibit delivery of pacing pulses when naturally occurring contractions are sensed. Also, demand mode may be a telemetrically programmable feature, allowing the pacemaker 20 to be switched into and out of demand mode when desired by a physician.

In order to regulate the rate at which the pacemaker 20 delivers pacing pulses to the heart 42, the processor 26 provides a rate control signal to the timing and control circuit 34. The rate control signal provided by the processor 26 preferably adjusts the escape interval used by the timing and control circuit 34, which has the effect of changing the maintained heart rate. Increasing the escape interval decreases the maintained heart rate, because the pacemaker 20 gives the heart 42 more time to contract on its own before the next pacing pulse is delivered. Decreasing the escape interval has the opposite effect.

Figure 2:
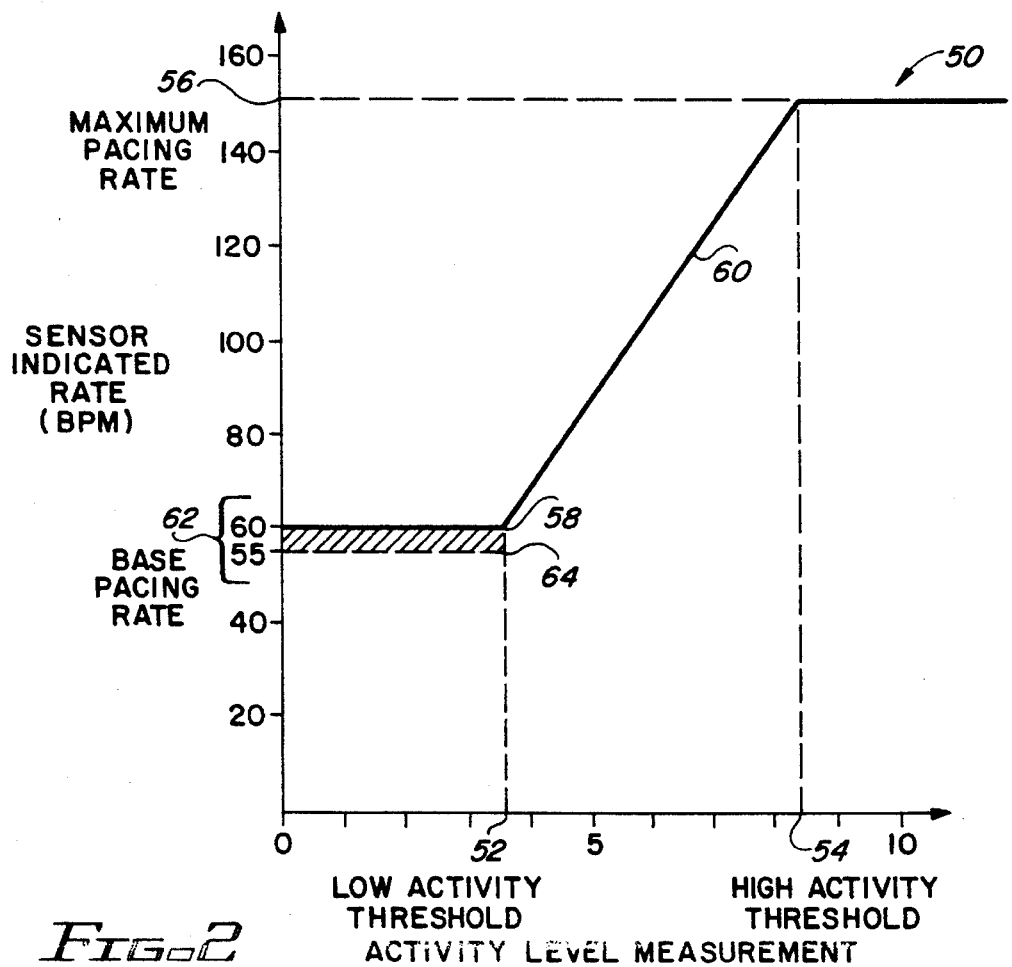
FIG. 2 generally illustrates the manner by which the rate-responsive pacemaker of FIG. 1 can modulate the base pacing rate of the transfer function in accordance with the principles of the present invention.

Referring now to FIG. 2, an illustrative transfer function 50 for a rate-responsive pacemaker is described so that the principles of the present invention may be better understood. The transfer function 50 may be used by the processor 26 (FIG. 1) to correlate activity level measurements (as derived by the processor 26 of FIG. 1) shown along the horizontal axis to sensor-indicated heart rates shown along the vertical axis.

Two activity levels are noted on the horizontal axis of the transfer function 50—a low activity threshold 52 and a high activity threshold 54. For activity level measurements above the high activity threshold 54, the pacing rate is maintained at a maximum pacing rate 56, shown in this case to be about 150 bpm. For activity level measurements between the low activity threshold 52 and the high activity threshold 54, the pacing rate preferably varies linearly between a resting rate 58 and the maximum pacing rate 56 in accordance with a transition segment 60 of the transfer function 50. The slope of the transition segment 60 defines the extent to which the pacing rate changes as the activity level measurement changes between the low activity threshold 52 and the high activity threshold 56.

The low activity threshold 52, the high activity threshold 54, the maximum pacing rate 56, the resting rate 58, and the slope of the transition segment 60 may be programmed into the memory 30 (FIG. 1) by the physician through the use of the programmer 38 (FIG. 1). Preferably, however, the low activity threshold 52 and the slope of the transition segment 60 are initially programmed by the physician, and then automatically adjusted by the processor 26 (FIG. 1) on a periodic basis, as described in the above-incorporated U.S. patent application Ser. No. 08/255,194, filed Jun. 7, 1994. Such periodic adjustments advantageously allow the pacemaker 20 (FIG. 1) to accommodate changes in the patient's lifestyle without the need for an unscheduled follow-up visit.

In accordance with the principles of the present invention, for any activity level measurement below the low activity threshold 52, the processor 26 (FIG. 1) sets the pacing rate to a rate defined by a varying base pacing rate 62. The varying base pacing rate 62 may be set by the processor 26 (FIG. 1) to rates that include the resting rate 58 (at the high end) and a sleeping rate 64 (at the low end). Preferably, the sleeping rate 64 is set by the physician to a rate that meets the patient's low metabolic demands during sleep (e.g., 55 bpm). The resting rate 58 (which may or may not be set by the physician) is preferably appropriate for when the patient is awake but relatively inactive. Thus, unlike many previously known pacemakers in which the base pacing rate is fixed, the pacemaker 20 (FIG. 1) of the present invention is capable of lowering the base pacing rate below the resting rate, so that the patient experiences greater comfort during sleep.

While operating in accordance with the transfer function 50, the processor 26 (FIG. 1) acquires digital data representative of the patient's activity level from the sensor circuitry 24 (FIG. 1). As explained above, the processor 26 (FIG. 1) uses this information to derive activity level measurements that it then uses to select an appropriate heart rate. In addition, certain activity level measurements are used by the processor 26 (FIG. 1) to derive activity variance measurements (in a manner described below). The activity variance measurements, in turn, are used by the processor 26 (FIG. 1)

to modulate the base pacing rate 62 of the transfer function 50.

Figure 3:
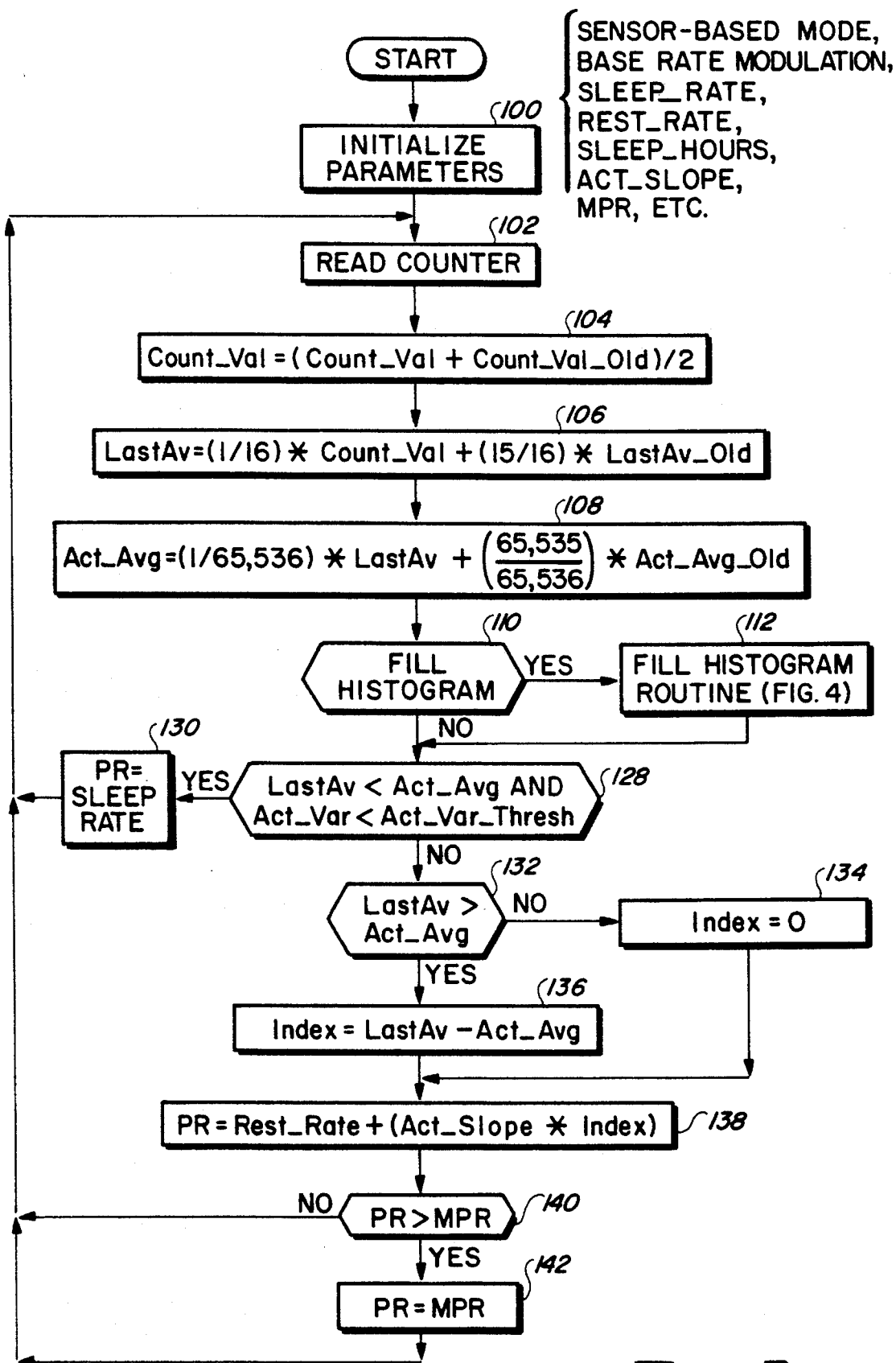
FIGS. 3 and 4 depict logic flow diagrams representing a first embodiment of a control program used by the processor shown in FIG. 1 to modulate the base pacing rate of the transfer function in accordance with the principles of the present invention.
Figure 4:
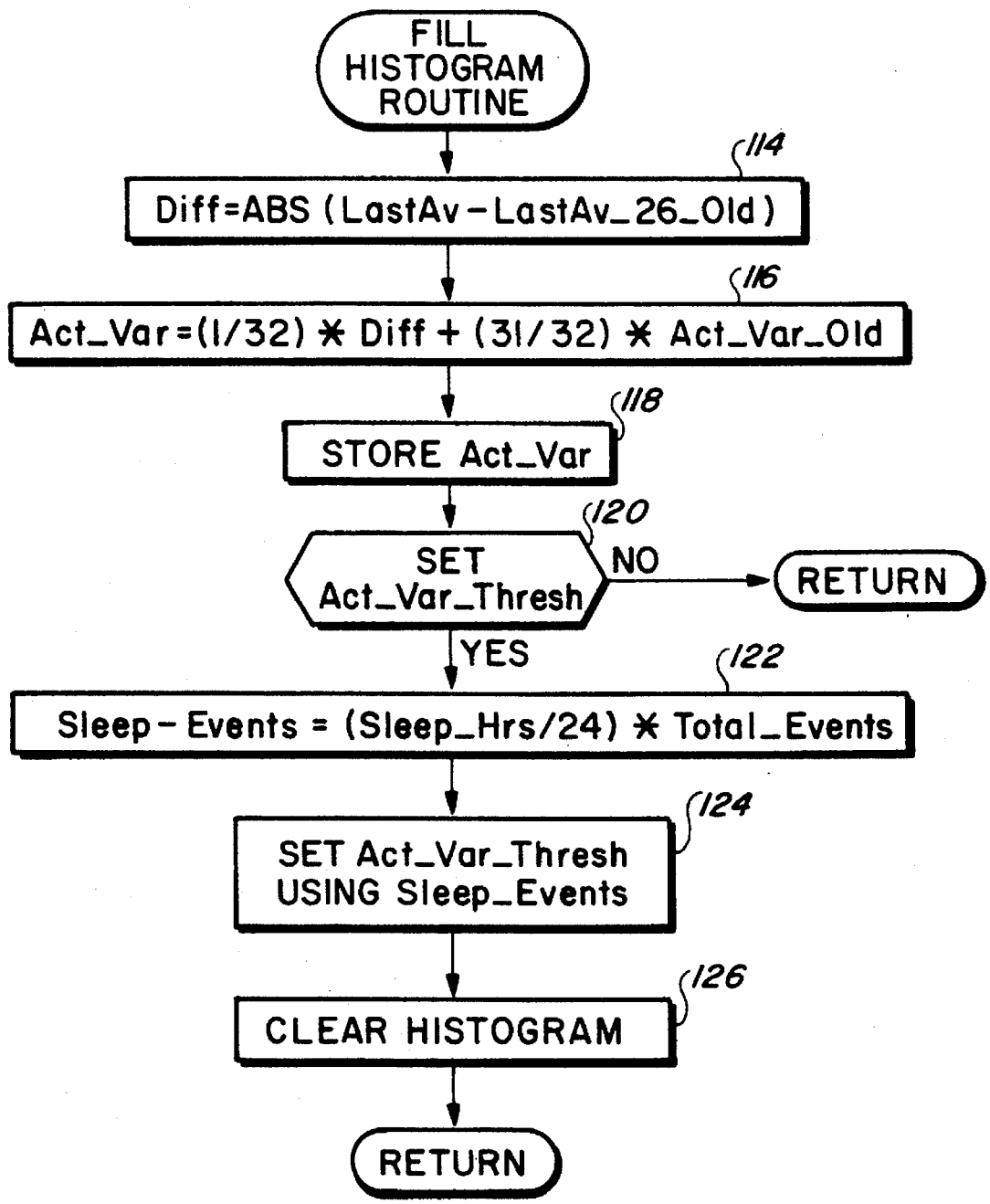

Referring now to FIGS. 3 and 4, a logic flow diagram is described which represents a first embodiment of a control program executed by the processor 26 of FIG. 1. The control program enables the pacemaker 20 (FIG. 1) to provide rate-responsive pacing therapy, and it also advantageously allows the pacemaker 20 (FIG. 1) to modulate the base pacing rate 62 (FIG. 2) of the transfer function 50 (FIG. 2). In this embodiment, the control program causes the processor 26 (FIG. 1) to switch the base pacing rate from a preprogrammed resting rate to a preprogrammed sleeping rate when the processor 26 (FIG. 1) determines that the patient has fallen asleep. The control program of FIGS. 3 and 4 also causes the processor 26 (FIG. 1) to switch the base pacing rate from the sleeping rate to the resting rate when the processor 26 (FIG. 1) determines that the patient is no longer sleeping. If the patient engages in physical activity, the control program causes the processor 26 (FIG. 1) to increase the pacing rate above the resting rate by an amount that accommodates the level of activity as measured by the sensor 22 (FIG. 1).

Referring first to FIG. 3, the control program starts when a start-up command is received from the external programmer 38 (FIG. 1) through the telemetry circuit 36 (FIG. 1). This command may be sent in connection with the implantation procedure (before, during, or after), and during subsequent follow-up visits.

After start-up, the processor 26 (FIG. 1) performs an initialization step 100, at which the pacemaker 20 (FIG. 1) acquires operating parameters from the external programmer 38 (FIG. 1) through the telemetry circuit 36 (FIG. 1), the parameters then being stored in the memory 30 (FIG. 1). Many of the parameters received at the step 100 may be conventional (e.g., pulse width, pulse amplitude, etc.); however, several other parameters are used to implement the features of the present invention. For example, at the step 100, the physician can disable base rate modulation, and can even disable rate-responsive pacing entirely. When a feature is disabled, the steps of the control program corresponding to those features are not performed by the processor 26 (FIG. 1).

The parameters that are used to implement base rate modulation also include sleeping rate (Sleep_Rate), resting rate (Rest_Rate), sleep hours (Sleep_Hrs), activity slope (Act_Slope), and maximum pacing rate (MPR). The sleeping rate is preferably set to a rate that comfortably meets the patient's low metabolic demands during sleep (e.g., 55 bpm). The resting rate is preferably set to a rate that is suitable for when the patient is awake but relatively inactive (e.g., 65 bpm). The number of sleep hours is set to the number of hours that the patient typically sleeps each day (e.g., 7 hours). The activity slope is preferably set initially to a level that allows the pacemaker 20 (FIG. 1) to provide sufficient increases (or decreases) to the pacing rate in accordance with increases (or decreases) in the activity level measurements (e.g., 0.6 bpm/count). Preferably, the processor 26 (FIG. 1) subsequently adjusts the activity slope in accordance with the patient's activity profile, as described in the above-incorporated U.S. patent application Ser. No. 08/255,194, filed Jun. 6, 1994. The maximum pacing rate is set to a rate that safely meets the patient's metabolic demands during high levels of exertion (e.g., 150 bpm).

After the step 100, the processor 26 (FIG. 1) performs a sequence of steps 102–108 which are preferably re-executed during each heartbeat interval. At the step 102, the processor 26 (FIG. 1) reads the contents of the counter (not shown) of the sensor circuit 24 (FIG. 1), and stores the value in a variable designated as Count_Val. As explained above, the contents of the counter are a digital representation of the patient's activity level as measured during a predetermined period (preferably 100 ms) within the current heartbeat interval, where about 62 counts corresponds to 1 G. At the step 102, the processor 26 (FIG. 1) also clears the counter in preparation for the next heartbeat interval.

In order avoid using a measurement that is uncharacteristically high or low, at the step 104, the processor 26 (FIG. 1) averages the current counter reading with the counter reading taken during the previous heartbeat interval, as shown in Equation 1.

$$\text{Count\_Val} = \frac{(\text{Count\_Val} + \text{Count\_Val\_Old})}{2} \tag{1}$$

The variable designated as Count_Val_Old is used to store the counter reading taken during the previous heartbeat cycle. However, during the first execution of the step 104 after start-up, Count_Val is effectively set equal to the current counter reading, since there is no previous counter reading to average it with.

At the step 106, the value stored in Count_Val is processed by the processor 26 (FIG. 1) using a recursive low-pass filter to derive a digitally smoothed representation of the patient's current activity level, as illustrated by Equation 2.

$$\text{LastAv} = (1/16) * \text{Count\_Val} + (15/16) * \text{LastAv\_Old} \tag{2}$$

The variable designated as LastAv contains the digitally smoothed representation of the patient's activity level. The variable designated as LastAv_Old represents the value of LastAv derived using Equation 2 during the previous cardiac cycle. At a heart rate of 72 bpm, the digital filter defined by Equation 2 has a time constant of approximately 13 seconds. During the first execution of the step 106, the variable LastAv is effectively set equal to the value of Count_Val.

At the step 108, the processor 26 (FIG. 1) uses the derived value of LastAv to derive the patient's average activity level, designated by the variable Act_Avg. This is accomplished by applying a recursive, low-pass digital filter to the value of LastAv, as illustrated by Equation 3.

$$\text{Act\_Avg} = (1/65536) * \text{LastAv} + (65535/65536) * \text{Act\_Avg\_Old} \tag{3}$$

The variable designated as Act_Avg_Old represents the value of Act_Avg derived during the previous heartbeat cycle. At a pacing rate of 60 bpm, the time constant of this digital filter is approximately 18 hours. Thus, the variable Act_Avg represents a running average of the patient's activity level, which in turn closely approximates the patient's activity level at rest. During the first execution of the step 108 after start-up, the value of Act_Avg is effectively set equal to the value of LastAv computed at the step 106.

After values have been computed for Count_Val, LastAv, and Act_Avg, the processor performs a test 110 to determine if it is time to store an activity variance measurement (computed as described below) in an activity variance histogram maintained in the memory 30 (FIG. 1). Preferably, the physician can select how frequently activity variance measurements are added to the histogram. In a preferred embodiment, an activity variance measurement is added to the histogram about once every 26 seconds, rather than every heartbeat cycle, in order to conserve space in the memory 30 (FIG. 1). As explained below, the activity variance histogram is used by the processor 26 (FIG. 1) to derive an activity variance threshold, which in turn is used to determine whether the patient is sleeping.

If the processor 26 (FIG. 1) determines at the test 110 that it is time to store an activity variance measurement in the histogram, a step 112 is performed, at which a Fill Histograms routine is called. The Fill Histograms routine is shown in FIG. 4.

The activity variance measurement to be stored in the activity variance histogram is derived by the processor 26 (FIG. 1) in accordance with steps 114 and 116. At the step 114, the processor 26 (FIG. 1) computes a value, designated by the variable Diff, representing the absolute value of the difference between the current value of LastAv and the value of LastAv that was computed about 26 seconds earlier, as illustrated in Equation 4.

$$\text{Diff}=\text{ABS}(\text{LastAv}-\text{LastAv\_26\_Old}) \quad (4)$$

The variable designated as LastAv_26_Old contains the value of LastAv computed about 26 seconds earlier. During the first execution of the step 114 after start-up, the value of Diff is set equal to zero.

The difference computed at the step 114 is digitally smoothed by the processor 26 (FIG. 1) at the step 116 using a recursive, low pass filter, as shown in Equation 5.

$$\text{Act\_Var}=(1/32)*\text{Diff}+(31/32)*\text{Act\_Var\_Old} \quad (5)$$

The variable designated as Act_Var is used to store the current smoothed difference, and the variable designated as Act_Var_Old is used to store the prior smoothed difference. During the first execution of the step 116 after start-up, the value of Act_Var is effectively set equal to the value of Diff.

At a step 118, the value of Act_Var computed at the step 116 is added to an appropriate bin of the activity variance histogram maintained in the memory 30 (FIG. 1). An activity variance histogram 210 containing data collected over a period of about one week for a typical patient is shown in FIG. 5.

Figure 5:
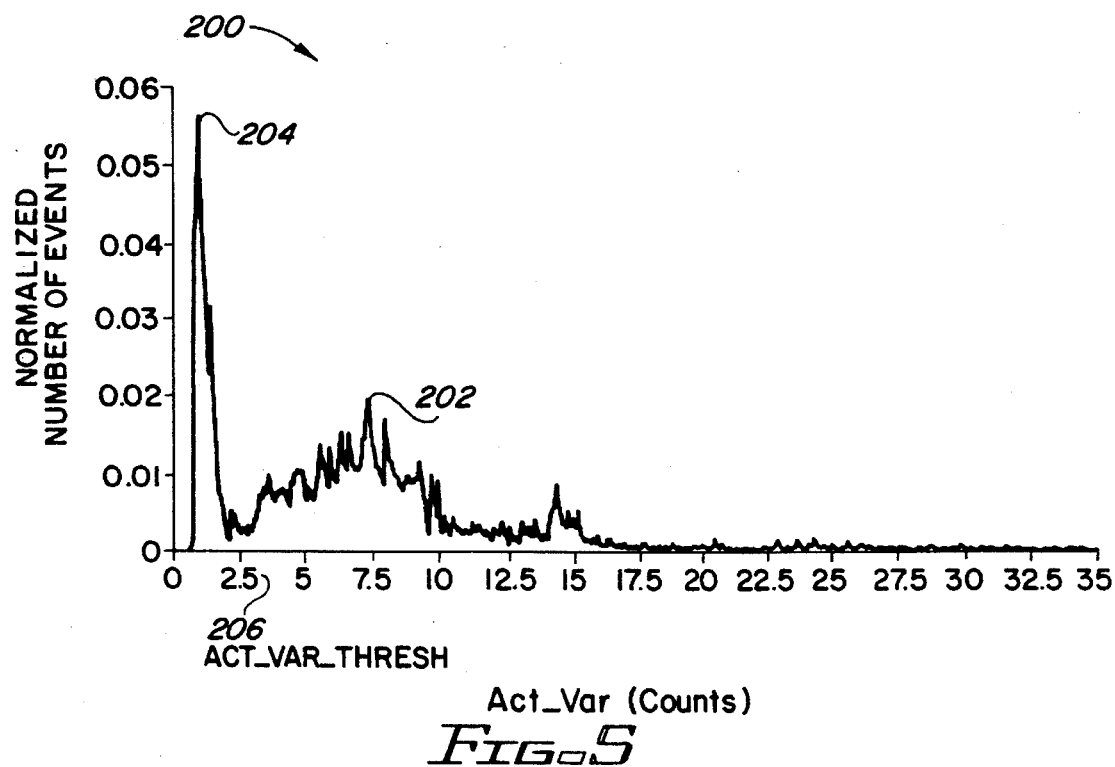
FIG. 5 depicts an illustrative activity variance histogram used by the processor shown in FIG. 1 to modulate the base pacing rate of the transfer function in accordance with the principles of the present invention.

Referring now to FIG. 5, the activity variance histogram 200 is preferably divided into 128 two-byte bins, each of which is assigned a corresponding Act_Var value. The activity variance histogram 200 therefore occupies 256 bytes of the memory 30 (FIG. 1).

The activity variance histogram 200 is characterized by a bimodal distribution. A higher mode 202 of the two modes corresponds to activity variance measurements derived during the day—while the patient was awake but relatively inactive. A lower mode 204, which is the dominant mode, corresponds to activity variance measurements derived during sleep.

A bin 206 of the activity variance histogram 200 is designated by the variable Act_Var_Thresh, corresponding to an activity variance measurement of about 2.5 counts. As explained below, the bin 206 is estimated to be the highest bin of the activity variance histogram 200 that contains activity variance measurements derived while the patient was sleeping.

Referring again to FIG. 4, after the activity variance measurement is stored in the activity variance histogram at the step 118, a test 120 is performed, where the processor 26 (FIG. 1) determines if it is time to determine an activity variance threshold, designated by the above-mentioned variable Act_Var_Thresh. Preferably, the activity variance threshold is re-evaluated on a weekly basis. If it is not time to determine the activity variance threshold, control returns to the main program of FIG. 4.

If it is time to determine the activity variance threshold, the processor 26 (FIG. 1) first estimates, at a step 122, the number of activity variance measurements stored in the activity variance histogram that were derived while the patient was sleeping. This value, designated by the variable Sleep_Events, is computed using Equation 6.

$$\text{Sleep\_Events}=(\text{Sleep\_Hrs}/24)*\text{Total\_Events} \quad (6)$$

The variable Sleep_Hrs represents the number of hours that the patient typically spends sleeping each day, as programmed by the physician at the initialization step 100 (FIG. 3). The variable Total_Events represents the total number of activity variance measurements stored in the activity variance histogram at the time the step 122 is performed. For a weekly histogram, there are about 23,296 total events.

At a step 124, the processor 26 (FIG. 1) uses the value of Sleep_Events from the step 122 to determine the activity variance threshold (Act_Var_Thresh). To accomplish this, the processor 26 (FIG. 1) adds the contents of the bins of the activity variance histogram, starting with the lowest bin and proceeding through successively higher bins until the number of measurements corresponding to the value of Sleep_Events have been counted. The bin at which counting stops is the bin that is deemed to be the highest bin containing activity variance measurements that were derived while the patient was sleeping. The variable Act_Var_Thresh is set equal to the activity variance value associated with this bin.

After the activity variance threshold is determined, the processor 26 (FIG. 1) clears the activity variance histogram at a step 126. The histogram is then ready to collect new data over the next week. Control then returns to the main program of FIG. 3.

Referring again to FIG. 3, the processor 26 (FIG. 1) proceeds to a test 128, where it performs a two-part test to determine if the patient is sleeping. Specifically, for the patient to be deemed asleep, the value of LastAv (derived at the step 106) must be less than the value of Act_Avg (derived at the step 108), and the value of Act_Var (derived at the step 116 (FIG. 4)) must be less than the value of Act_Var_Thresh (determined at the step 124 (FIG. 4)). Essentially, this test determines if the patient's current level of activity is below the average level of activity, and if the patient's most recent activity variance measurement is below the most recently determined activity variance threshold. If both conditions are met, the processor 26 (FIG. 1) proceeds to a step 130, where it sets the pacing rate (PR) to the value of Sleep_Rate. The processor 26 (FIG. 1) preferably sets the pacing rate to the lower level for the current heartbeat cycle by instructing the timing and control circuit 34 (FIG. 1) to increase the escape interval.

If either condition of the test 128 is not met, a test 132 is performed, where the processor 26 (FIG. 1) determines whether the value of LastAv exceeds the value of Act_Avg (i.e., whether the patient's current level of activity exceeds the average level of activity). If not, the patient is deemed to be at rest (but awake), and accordingly, the processor 26 (FIG. 1) proceeds to a step 134 where it sets a variable designated as Index equal to zero. (As described below, the variable Index is used by the processor 26 (FIG. 1) to increase the PR above the resting rate.) Otherwise, the processor 26 (FIG. 1) proceeds to a step 136 where it sets the value of Index equal to the difference between the values of LastAv and Act_Avg, as illustrated by Equation 7.

$$\text{Index}=(\text{LastAv}-\text{Act\_Avg}) \quad (7)$$

The variable Index represents an instantaneous relative activity level measurement, which may be used to define a pacing rate for the current cardiac cycle. More precisely, the value of Index represents the amount by which the patient's current level of physical activity exceeds the average level of activity, as defined by the variable Act_Avg.

The processor 26 (FIG. 1) then proceeds to a step 138 where it computes an appropriate PR using the preprogrammed resting rate (Rest_Rate), the preprogrammed (or automatically determined) activity slope (Act$_{13}$Slope), and the value of Index derived at the step 136, as illustrated by Equation 8.

$$PR=Rest\_Rate+(Act\_Slope*Index) \qquad (8)$$

Through the operation of Equation 8, the PR is increased from the resting rate by an amount defined by the product of the activity slope and the current value of the variable Index. Thus, if the patient is awake but relatively inactive (which usually corresponds to an average level of activity as defined by the variable Act_Avg) the PR is set to the value of Rest_Rate, because the value of Index is zero. As the patient becomes more active, the value of Index increases from zero, resulting in a corresponding increase in the PR. In order to avoid sudden changes in the patient's heart rate, reaction and recovery times may be applied to the Index value before it is used to derive the PR, as described in the above-incorporated U.S. patent application Ser. No. 08/255,194, filed Jun. 7, 1994.

Then, at a test 140, the processor 26 (FIG. 1) determines whether the PR derived at the step 138 exceeds the preprogrammed MPR. If so, the PR is set to the MPR at a step 142. Otherwise, the PR remains at the rate set at the step 138. After a pacing pulse is delivered (if required) in accordance with the newly determined PR (preferably by adjusting the escape interval), the program loops back to the step 102 to begin the next heartbeat cycle.

Figure 6:
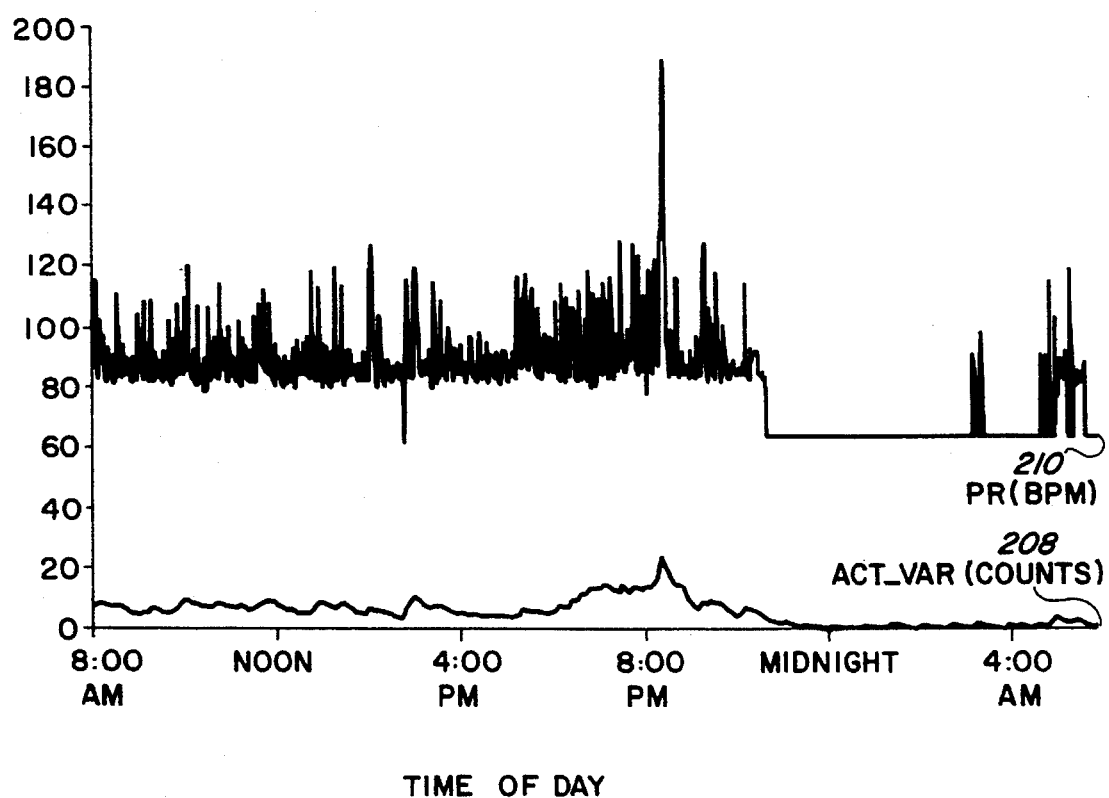
FIG. 6 is a graph depicting a plot of pacing rates, and a plot of activity variance measurements used by the processor shown in FIG. 1 to derive the pacing rates, in accordance with the first embodiment of the control program shown in FIGS. 3 and 4.

The manner by which base rate modulation is accomplished in accordance with the first embodiment of the invention may be understood by reference to the graph shown in FIG. 6. In FIG. 6, a plot 208 of activity variance measurements derived by the processor 26 (FIG. 1) over a 24 hour period using the control program of FIGS. 3 and 4 is shown on the same time line as a plot 210 of pacing rates derived using the plotted activity variance measurements. From about 8:00 AM to about 11:00 PM, while the subject is awake and occasionally active, the activity variance measurements range from about 5 counts to about 25 counts. During this time period, the pacing rate exhibits significant variations; however, it does not fall below the resting rate, which in this example is set to about 80 bpm. Also, it should be noted that during the same period, each excursion in the plot 210 of heart rates rapidly returns to the resting rate.

At about 11:00 PM, when the subject falls asleep, the plot 208 shows that the activity variance measurements substantially decline—to a level that is below the current activity variance threshold. During the same period, the subject's activity level measurements fall below the subject's average level of activity (although this is not shown in FIG. 6). Accordingly, the pacing rate decreases to the sleeping rate, which in this example is set to about 65 bpm. For most of the period from about 11:00 PM to about 5:00 AM, the pacing rate is maintained at the sleeping rate, with some variation at about 3:00 AM (the result of a brief period of activity). Thus it is seen that the control program of FIGS. 3 and 4 effectively provides the pacemaker 20 (FIG. 1) with the capability of detecting when the subject has fallen asleep, and of reducing the pacing rate to a level that comfortably meets the subject's low metabolic demands during sleep.

Figure 7:
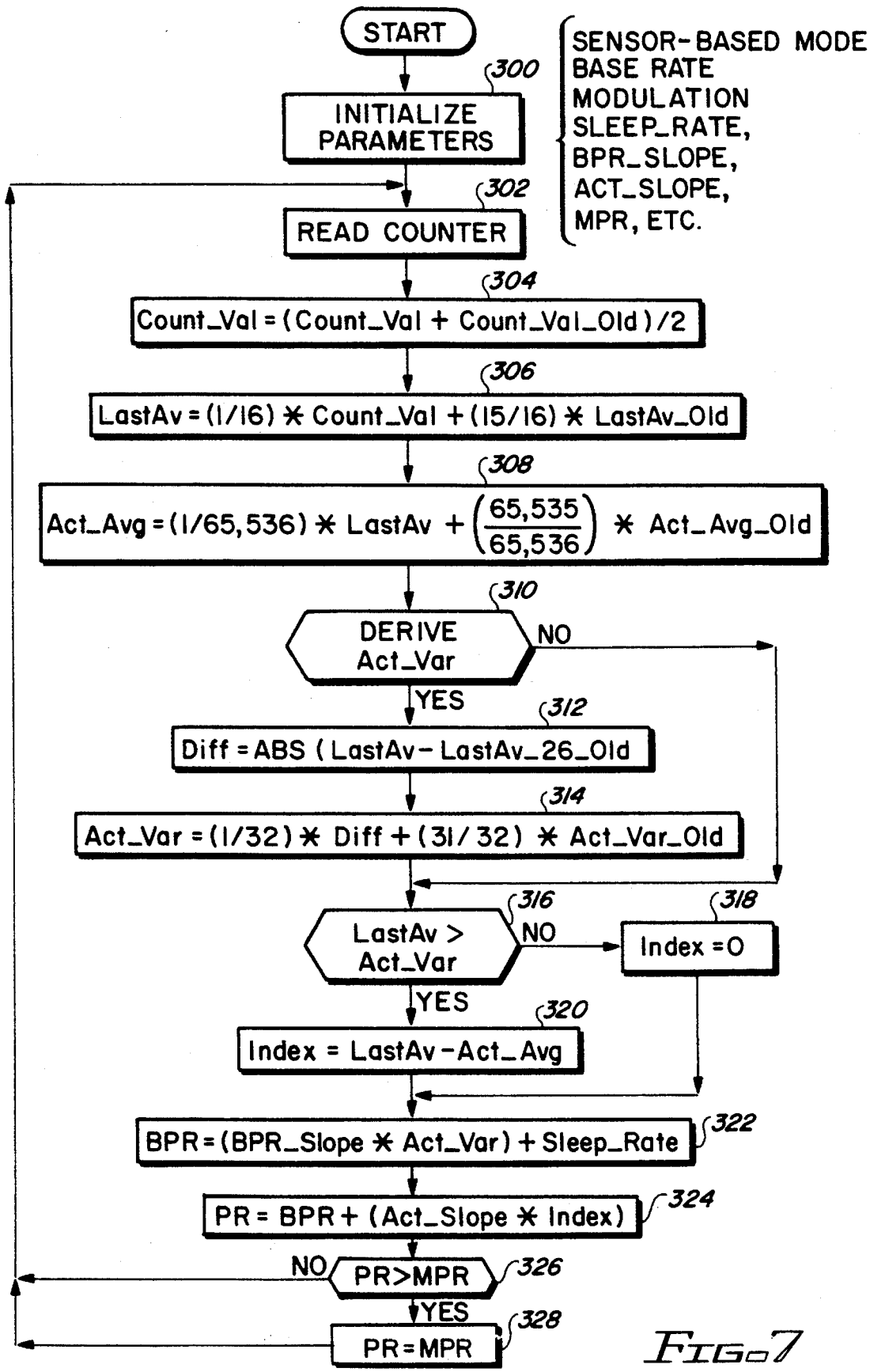
FIG. 7 depicts a logic flow diagram representing a second embodiment of a control program used by the processor shown in FIG. 1 to modulate the base pacing rate of the transfer function in accordance with the principles of the present invention.

Referring now to FIG. 7, a logic flow diagram is described which represents a second embodiment of a control program executed by the processor 26 (FIG. 1). The control program of FIG. 7 also advantageously allows the pacemaker 20 (FIG. 1) to modulate the base pacing rate 62 (FIG. 2) of the transfer function 50 (FIG. 1); however, it differs from the control program of FIGS. 3 and 4 in several respects. For example, in this embodiment, the processor 26 (FIG. 1) does not simply switch the base pacing rate between a sleeping rate and a resting rate. Rather, the processor 26 (FIG. 1) can use activity variance measurements to set the pacing rate to rates between a sleeping rate and a resting rate. More accurately, although the base pace rate is bounded on its low end by a preprogrammed sleeping rate, in this embodiment, the base pacing rate has no predetermined upper limit (i.e., no predetermined resting rate). Also, an activity variance histogram is not required. Instead, a preprogrammed base rate slope is applied to the activity variance measurements to determine the amount by which the base pacing rate should be increased above the sleeping rate.

After the control program of FIG. 7 is started (via a command from the programmer 38 (FIG. 1)), the processor 26 (FIG. 1) performs an initialization step 300, where it acquires appropriate pacing parameters. For this embodiment, the parameters used to implement base rate modulation include the sleeping rate (Sleep_Rate), the activity slope (Act_Slope), and the maximum pacing rate (MPR), which are described above in connection with FIG. 3. However, the activity slope is preferably set to a lower level than previously described (e.g., 0.3 bpm/count), because in this embodiment, the base pacing rate may contribute to the rate response of the pacemaker 20 (FIG. 1) when the patient engages in activity. Another parameter defined at the step 300 is the base rate slope (BPR_Slope), which is preferably set to a value that permits gradual changes to the base pacing rate in response to changes in the activity variance measurements (e.g., 2.8 bpm/count).

After the initialization step 300, the processor 26 (FIG. 1) performs a sequence of steps 302–308 to define variables that are described above in connection with FIG. 3. At the step 302, the processor 26 (FIG. 1) sets the variable Count_Val to the contents of the counter (not shown) of the sensor circuit 24 (FIG. 1), as described above for the step 102 (FIG. 3). At the step 304, the current value of Count_Val is averaged with the value from the previous heartbeat cycle, as illustrated above by Equation 1. The processor 26 (FIG. 1) then digitally filters the averaged value of Count_Val at the step 306, as illustrated above by Equation 2, in order to derive an activity level measurement, designated by the variable LastAv. Then, at the step 308, the value of LastAv is digitally filtered, as illustrated above by Equation 3, in order to derive the patient's average level of activity, designated by the variable Act_Avg.

At a test 310, the processor 26 (FIG. 1) determines whether it is time to derive an activity variance measurement, designated by the variable Act_Var. Preferably, an activity variance measurement is computed about every 26 seconds. If it is time to compute an activity variance measurement, the processor 26 (FIG. 1) performs a step 312 where a variable Diff is set equal to the absolute value of the difference between the current value of LastAv and the value of LastAv computed about 26 seconds earlier, as illustrated above by Equation 4. The value of Diff is then digitally filtered at a step 314, as illustrated above by Equation 5, to derive the activity variance measurement, Act_Var.

At a test 316, the processor 26 (FIG. 1) determines whether the value of LastAv (derived at the step 306) exceeds the value of ActAvg (derived at the step 308) (i.e., whether the patient's current level of activity exceeds the patient's average level of activity). If not, the processor 26 (FIG. 1) proceeds to a step 318 where it sets a variable designated as Index equal to zero. Otherwise, the processor 26 (FIG. 1) proceeds to a step 320 where it sets the value of Index equal to the difference between the values of LastAv and Act_Avg, as illustrated above by Equation 7.

At a step 322, the processor 26 (FIG. 1) derives the base pacing rate (BPR) using the value of Act_Var computed at the step 314, and the preprogrammed values of BPR_Slope and Sleep_Rate, as illustrated by Equation 9.

$$BPR = Sleep\_Rate + (BPR\_Slope * Act\_Var) \qquad (9)$$

Through the use of Equation 9, the processor 26 (FIG. 1) advantageously modulates the BPR from the sleeping rate to higher rates that are appropriate for when the patient is awake but relatively inactive. As the activity variance measurements approach zero, the BPR approaches its lower limit—the sleeping rate. Although Equation 9 does not impose an upper limit on the BPR, a practical consequence of Equation 9 is that the second term contributes modestly to the overall pacing rate (e.g., about 0–15 bpm), as long as the BPR_Slope is chosen properly. Thus, the BPR derived in accordance with Equation 9 reaches, at its higher end, rates that are suitable as resting rates.

At a step 324, the processor 26 (FIG. 1) derives the pacing rate (PR) using the BPR from the step 322, the preprogrammed (or automatically determined) activity slope (Act_Slope), and the value of Index derived at the step 320, as illustrated by Equation 10.

$$PR = BPR + (Act\_Slope * Index) \qquad (10)$$

To avoid sudden changes in the PR, reaction and recovery times may be applied to the Index value before it is used in Equation 10.

When the steps 322 and 324 are viewed in combination, it should be apparent that three terms contribute to the total PR defined by Equation 10. The first term (Sleep_Rate) defines the sleeping rate, which is the minimum heart rate that the pacemaker 20 (FIG. 1) allows the patient to experience. The second term (the product of BPR_Slope and Act_Var) is used to modulate the BPR from the sleeping rate to higher rates that are suitable as resting rates. The third term (the product of Act_Slope and Index) is used to increase the pacing rate above the varying BPR to rates that accommodate the patient's level of activity.

At a test 326, the processor 26 (FIG. 1) determines whether the PR derived at the step 324 exceeds the preprogrammed MPR. If so, the PR is set to the MPR at a step 328. Otherwise, the PR remains at the rate set at the step 324. After a pacing pulse is delivered (if required) in accordance with the newly determined PR (preferably by adjusting the escape interval), the program loops back to the step 302 to begin the next heartbeat cycle.

Figure 8:
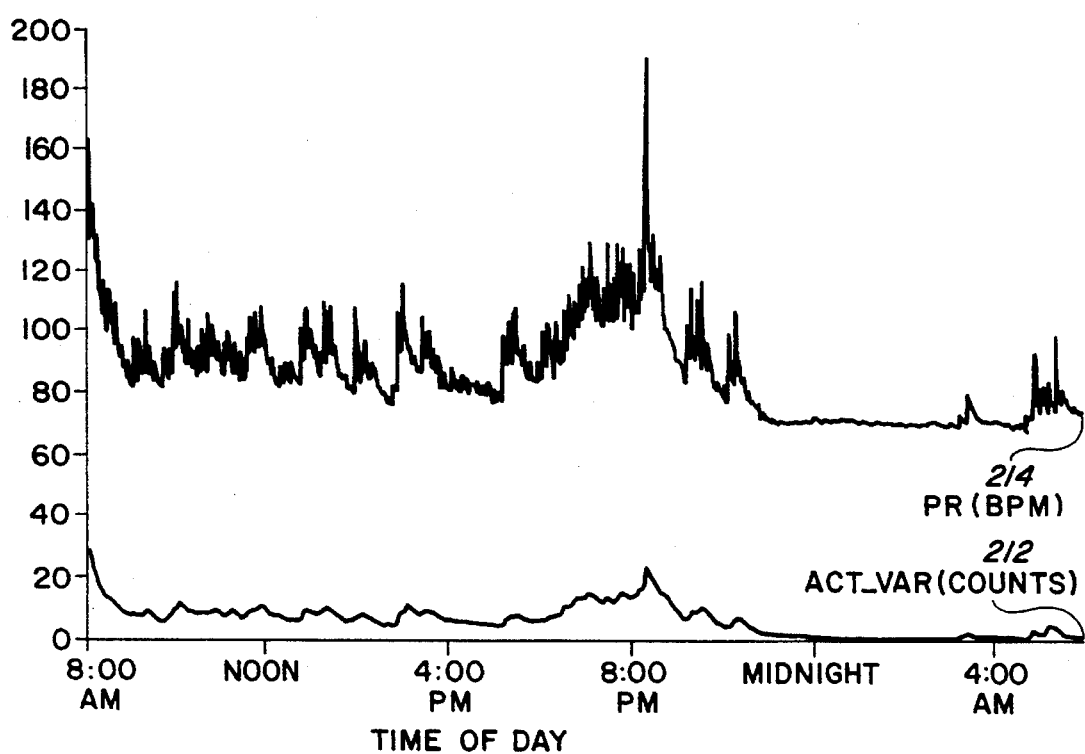
FIG. 8 is a graph depicting a plot of pacing rates, and a plot of activity variance measurements used by the processor shown in FIG. 1 to derive the pacing rates, in accordance with the second embodiment of the control program shown in FIG. 7.

Referring now to FIG. 8, a plot 212 of activity variance measurements (derived in accordance with the step 314 of FIG. 7) is shown along with a plot 214 of pacing rates derived in accordance with the second embodiment of the control program using the plotted activity variance measurements. Like the graph described in connection with FIG. 6, the plots 212 and 214 exhibit a pronounced transition when the subject falls asleep at about 11:00 PM. However, there are clear distinctions between the two graphs.

First, the plot 214 of pacing rates is not limited at its low end to a clearly defined resting rate while the subject is awake, as is the case for the plot 210 of FIG. 6. Instead, the second embodiment of the control program causes the base pacing rate to gradually transition through a range of rates that are suitable for when the subject is at rest. A related distinction is that for this embodiment, the pacing rates gradually transition from higher rates associated with activity to lower rates suitable for rest (unlike the plot 210 of FIG. 6, which shows rapid transitions between pacing rates associated with activity and the resting rate).

Second, the transition from the pacing rates derived while the subject was awake to the sleeping rate at about 11:00 PM is much more gradual than that shown in FIG. 6 for the first embodiment. More gradual transitions may be desirable for some patients. The second embodiment advantageously provides this feature without using reaction and recovery times.

Figure 9:
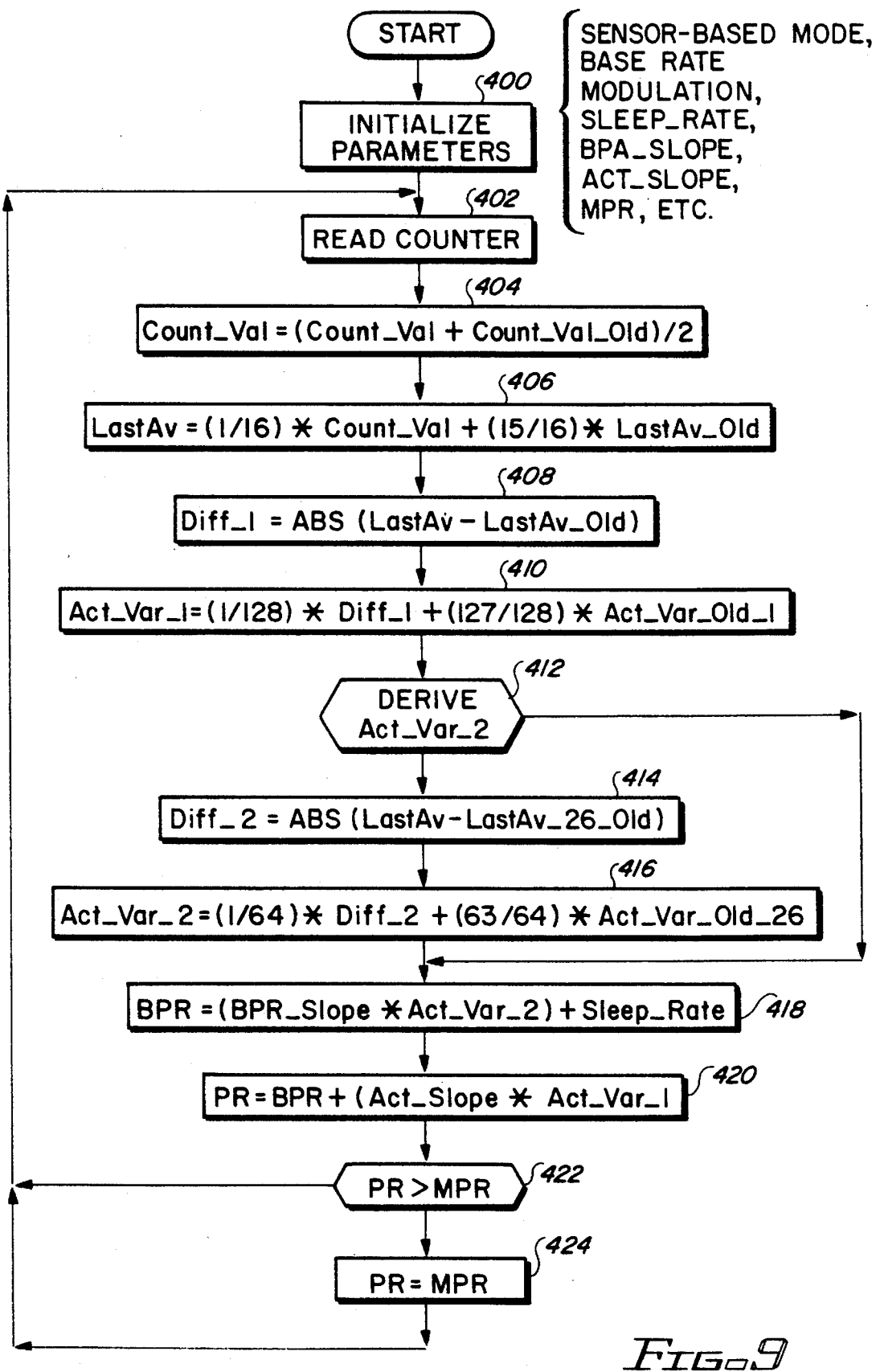
FIG. 9 depicts a logic flow diagram representing a third embodiment of a control program used by the processor shown in FIG. 1 to modulate the base pacing rate of the transfer function in accordance with the principles of the present invention.

Referring now to FIG. 9, a logic flow diagram is described which represents a third embodiment of a control program executed by the processor 26 (FIG. 1). Like the second embodiment, the control program of FIG. 9 also uses a three-term transfer relation to derive the pacing rate in accordance with the patient's metabolic demands. One of the three terms advantageously modulates the base pacing rate (BPR), again using activity variance measurements, without the need for a preprogrammed upper limit on the BPR (i.e., a preprogrammed resting rate). However, unlike the second embodiment, the control program of FIG. 9 does not directly use activity level measurements to determine the amount by which the pacing rate should be increased above the BPR. Instead, activity variance measurements are used, but they are computed somewhat differently than the activity variance measurements used to modulate the BPR.

After the control program of FIG. 7 is started (via a command from the programmer 38 (FIG. 1)), the processor 26 (FIG. 1) performs an initialization step 400, where it acquires appropriate pacing parameters. Like the second embodiment, the required parameters include (in addition to conventional parameters) the sleeping rate (Sleep_Rate), the base rate slope (BPR_Slope), the activity slope (Act_Slope), and the maximum pacing rate (MPR). For this embodiment, the base rate slope is preferably set to about 2.5 bpm/count, and the activity slope is preferably set to about 0.6 bpm/count.

After the initialization step 400, the processor 26 (FIG. 1) performs a sequence of steps 402–406 to define variables that are described above in connection with FIG. 3. At the step 402, the processor 26 (FIG. 1) sets the variable Count_Val to the contents of the counter (not shown) of the sensor circuit 24 (FIG. 1), as described above for the step 102 (FIG. 3). At the step 404, the current value of Count_Val is averaged with the value from the previous heartbeat interval, as illustrated above by Equation 1. The processor 26 (FIG. 1) then digitally filters the averaged value of Count_Val at the step 406, as illustrated above by Equation 2, in order to derive an activity level measurement, designated by the variable LastAv.

In this embodiment, the patient's average level activity is not used. Instead, the processor 26 (FIG. 1) proceeds to a step 408 where it computes a value, designated by the variable $Diff_1$, representing the absolute value of the difference between the current value of LastAv and the value of LastAv that was computed during the preceding heartbeat cycle, as illustrated by Equation 11.

$$Dif\_1 = ABS(LastAv - LastAv\_Old) \qquad (11)$$

The variable designated as LastAv_Old contains the value of LastAv computed during the preceding heartbeat cycle. During the first execution of the step 408, the value of Diff_1 is set equal to zero.

At a step 410, the processor 26 (FIG. 1) derives a first activity variance measurement (which, as explained below, is used to adjust the pacing rate to accommodate increased or decreased levels of activity) by digitally filtering the difference computed at the step 408 using a recursive, low pass filter, as shown in Equation 12.

$$\text{Act\_Var\_1}=(1/128)*\text{Diff\_1} \qquad (12)$$

The variable designated as Act_Var_1 is used to store the current value of the first activity variance measurement. The variable designated as Act_Var_1 is used to store the value of the first activity variance measurement derived during the preceding heartbeat cycle. At pacing rate of 72 bpm, the time constant of the digital filter defined by Equation 12 is about 1.6 minutes. The rather short time constant allows the variable Act_Var_1 to reflect short-term changes in the patient's current level of activity. During the first execution of the step 410, the value of Act_Var_1 is effectively set equal to the value of Diff_1.

At a test 412, the processor 26 (FIG. 1) determines whether it is time to derive a second activity variance measurement, designated by the variable Act_Var_2, which is used to modulate the BPR. Preferably, Act_Var_2 is recomputed about every 26 seconds. If it is time to compute the second activity variance measurement, the processor 26 (FIG. 1) proceeds to a step 414 where it computes a value, designated by the variable Diff_2, representing the absolute value of the difference between the current value of LastAv and the value of LastAv that was computed about 26 seconds earlier, as illustrated by Equation 13.

$$\text{Diff\_2}=\text{ABS}(\text{LastAv}-\text{LastAv\_26\_Old}) \qquad (13)$$

The variable designated as LastAv_26_Old contains the value of LastAv computed about 26 seconds earlier. During the first execution of the step 414, the value of Diff_2 is set equal to zero.

At a step 416, the processor 26 (FIG. 1) derives the second activity variance measurement (which, as explained below, is used to modulate the BPR) by digitally filtering the difference computed at the step 414 using a recursive, low pass filter, as shown in Equation 14.

$$\text{Act\_Var\_2}=(1/64)*\text{Diff\_2}+(63/64)*\text{Act\_Var\_Olde\_26} \qquad (14)$$

The variable designated as Act_Var_2 is used to store the current value of the second activity variance measurement. The variable designated as Act_Var_$_{Old}$_26 is used to store the value of the second activity variance measurement derived about 26 seconds earlier. At pacing rate of 72 bpm, the time constant of the digital filter defined by Equation 14 is about 38 minutes. The long time constant causes the variable Act_Var_2 to resist varying in response to short-term changes in the patient's activity level. During the first execution of the step 416, the value of Act_Var_2 is effectively set equal to the value of Diff_2.

At a step 418, the processor 26 (FIG. 1) derives the base pacing rate (BPR) using the value of Act_Var_2 computed at the step 416, and the preprogrammed values of BPR_Slope and Sleep_Rate, as illustrated by Equation 15.

$$\text{BPR}=\text{Sleep\_Rate}+(\text{BPR\_Slope}*\text{Act\_Var\_2}) \qquad (15)$$

Through the use of Equation 15, the processor 26 (FIG. 1) advantageously modulates the BPR from the sleeping rate to higher rates that are appropriate for when the patient is awake but relatively inactive. As the second activity variance measurement approaches zero, the BPR approaches its lower limit—the sleeping rate. Like the second embodiment, Equation 15 does not impose an upper limit on the BPR. However, the practical consequence of Equation 15 is that the second term contributes modestly to the overall pacing rate (e.g., about 0–15 bpm), as long as the BPR_Slope is chosen properly. Thus, for practical purposes, the BPR derived in accordance with Equation 15 reaches, at its higher end, rates that are suitable as resting rates.

At a step 420, the processor 26 (FIG. 1) derives the pacing rate (PR) using the BPR from the step 322, the preprogrammed activity slope (Act_Slope), and the first activity variance measurement (Act_Var_1) derived at the step 410, as illustrated by Equation 16.

$$\text{PR}=\text{BPR}+(\text{Act\_Slope}*\text{Act\_Var\_1}) \qquad (16)$$

In a manner similar to that described for the second embodiment, three terms contribute to the PR derived using Equation 16. The first term (Sleep_Rate) defines the sleeping rate, which is the minimum heart rate that the pacemaker 20 (FIG. 1) allows the patient to experience. The second term (the product of BPR_Slope and Act_Var_2) is used to modulate the BPR from the sleeping rate to higher rates that are suitable as resting rates. Using the second activity variance measurements in this way leads to a relatively stable BPR, because of the long time constant of Equation 14. The third term (the product of Act_Slope and Act_Var_1) is used to increase the pacing rate above the varying BPR to rates that accommodate the patient's level of activity. In contrast to the second activity variance measurements, the first activity variance measurements are appropriate for deriving activity-based pacing rates, because the relatively short time constant of Equation 12 causes the first activity variance measurements to reflect short-term changes in the patient's activity level.

At a test 422, the processor 26 (FIG. 1) determines whether the PR derived at the step 420 exceeds the preprogrammed MPR. If so, the PR is set to the MPR at a step 424. Otherwise, the PR remains at the rate set at the step 420. After a pacing pulse is delivered (if required) in accordance with the newly determined PR (preferably by adjusting the escape interval), the program loops back to the step 402 to begin the next heartbeat cycle.

Figure 10:
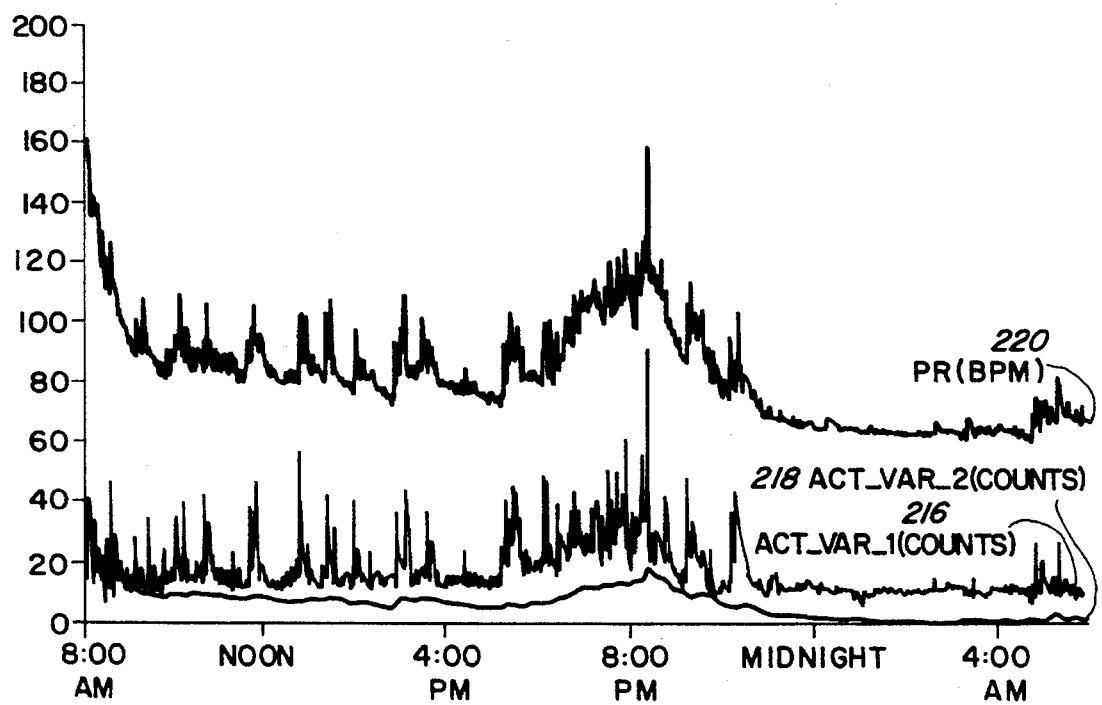
FIG. 10 is a graph depicting a plot of pacing rates, and plots of activity variance measurements used by the processor shown in FIG. 1 to derive the pacing rates, in accordance with the third embodiment of the control program shown in FIG. 9.

Referring now to FIG. 10, a plot 216 of first activity variance measurements (derived in accordance with the step 410 of FIG. 9) and a plot 218 of second activity variance measurements (derived in accordance with the step 416 of FIG. 9) are shown along with a plot 220 of pacing rates derived in accordance with the third embodiment of the control program using the plotted first and second activity variance measurements. Like the graph described in connection with FIG. 8 for the second embodiment, the plot 220 of pacing rates exhibits gradual transitions through a range of rates that are suitable for when the subject is at rest. Also, the plot 220 of pacing rates gradually transitions from higher rates associated with activity to lower rates suitable for rest. Further, the transitions to and from the sleeping rate (i.e., at about 11:00 PM and about 5:00 AM) are more gradual than those exhibited in FIG. 6 for the first embodiment.

FIG. 10 also illustrates the impact of the time constants on the first and second activity variance measurements. The plot 218 of second activity variance measurements does not exhibit severe fluctuations, even while the subject is awake. This characteristic renders the second activity variance measurements, derived using the long time constant, particularly suitable for modulating the base pacing rate, while at the same time maintaining base rate stability. On the other hand, the plot 216 of first activity variance measurements exhibits significant variations in response to patient activity, rendering this parameter suitable for deriving the activity-based portion of the pacing rate.

Thus, a system and method for modulating the base rate of a transfer function for a rate-responsive pacemaker are provided. One skilled in the art will appreciate that the present invention can be practiced by other than the described embodiments, which are presented for the purposes of illustration and not of limitation, and the present invention is limited only by the claims that follow.

What is claimed is:

1. A rate-responsive pacemaker for administering pacing pulses to a patient's heart, the pacemaker including memory means for storing a predetermined transfer function that correlates sensor level measurements representative of the patient's metabolic need to heart rate, the predetermined transfer function being characterized by a base pacing rate, a maximum pacing rate, and a transition segment defining pacing rates between the base pacing rate and the maximum pacing rate, the rate-responsive pacemaker comprising:

a pulse generator for generating pacing pulses at a selectable rate between the base pacing rate and the maximum pacing rate in accordance with the predetermined transfer curve;

a physiological sensor for generating raw sensor signals indicative of the patient's level of metabolic need;

a processor, coupled to the pulse generator and the physiological sensor, for controlling the rate of pacing pulses, the processor including:
(a) means for processing the raw sensor signals to derive the sensor level measurements;
(b) means for determining an appropriate heart rate for the patient's level of metabolic need based on the sensor level measurements and the corresponding heart rate defined by the predetermined transfer function;
(c) means for causing the pulse generator to generate pacing pulses at the appropriate heart rate;
(d) means for deriving first variance measurements based on the sensor level measurements, the first variance measurements being based on the difference between a current sensor level measurement and at least one earlier sensor level measurement; and
(e) means for modulating the base pacing rate in accordance with the first variance measurements.

2. The pacemaker of claim 1, wherein:

the memory further includes means for storing a resting rate and a sleeping rate that is lower than the resting rate; and the modulating means includes means for modulating the base pacing rate between the resting rate and the sleeping rate.

3. The pacemaker of claim 2, wherein:

the memory further includes means for storing a sensor measurement threshold and a variance measurement threshold; and the processor includes means for setting the base pacing rate to the sleeping rate when a current sensor measurement is below the sensor measurement threshold and a current first variance measurement is below the variance measurement threshold.

4. The pacemaker of claim 3, wherein the processor includes means for setting the base pacing rate to the resting rate when either the current sensor measurement meets or exceeds the sensor measurement threshold, or the current first variance measurement meets or exceeds the variance measurement threshold.

5. The pacemaker of claim 3, wherein the processor includes means for maintaining a running average of the sensor measurements in the memory, the running average defining the sensor measurement threshold.

6. The pacemaker of claim 5, wherein the processor includes means for maintaining the running average by digitally filtering the sensor measurements using a time constant of about 18 hours.

7. The pacemaker of claim 3, wherein:

the memory includes means for storing first variance measurements derived during a predetermined period of time as a histogram, the histogram including a plurality of bins ranging from a lowest bin to a highest bin, each bin being associated with a different first variance measurement value; and the processor includes means for deriving the variance measurement threshold by determining a bin associated with the highest first variance measurement derived while the patient was sleeping.

8. The pacemaker of claim 7, wherein:

the memory further includes means for storing a value representing a fraction of time that the patient sleeps each day;

the processor includes means for maintaining a value in the memory representing a total number of first variance measurements stored in the memory during the predetermined period of time; and the processor includes means for deriving the highest first variance measurement derived while the patient was sleeping by:

estimating a number of first variance measurements that were derived while the patient was sleeping during the predetermined period of time in accordance with the stored fraction of time that the patient sleeps each day and the stored total number of first variance measurements; and counting the first variance measurements stored in the histogram, starting with the lowest bin and proceeding through successively higher bins until the estimated number of first variance measurements that were derived while the patient was sleeping have been counted, the bin associated with the last count defining the highest first variance measurement derived while the patient was sleeping.

9. The pacemaker of claim 7, wherein the patient predetermined period of time is about one week.

10. The pacemaker of claim 1, wherein the processor includes means for deriving each first variance measurement by taking an absolute value of a difference between a current sensor measurement and an earlier sensor measurement, and filtering the result with a recursive, low pass digital filter.

11. The pacemaker of claim 10, wherein the current sensor measurement is derived by the processor about 26 seconds after the processor derives the earlier sensor measurement.

12. The pacemaker of claim 1, wherein:

the memory includes means for storing a base rate slope and a sleeping rate that defines a minimum heart rate maintained by the pacemaker; and the the base pacing rate by increasing the base pacing rate from the sleeping rate by an amount defined by the product of the base rate slope and the first variance measurements.

13. The pacemaker of claim 12, wherein:

the sensor measurements derived by the processor comprise second variance measurements; and the processor includes means for correlating the second variance measurements to the transition segment of the transfer function to derive to determine the appropriate heart rate for the patient's level of metabolic need.

14. The pacemaker of claim 13, wherein:

the memory further includes means for storing an activity slope that defines the transition segment of the transfer function; and the processor includes means for deriving the appropriate heart rate by increasing the heart rate from the base pacing rate by an amount defined by the product of the activity slope and the second variance measurements.

15. The pacemaker of claim 13, wherein the first variance measurement exhibit less variation over time than the second variance measurements.

16. The pacemaker of claim 1, wherein:

the physiological sensor comprises an activity sensor; and the sensor measurements derived by the processor represent levels of physical activity, the levels of physical activity being indicative of the levels of metabolic need.

17. A method of providing rate-responsive pacing therapy to a patient's heart in an implantable stimulation device, the implantable stimulation device including memory means for storing a predetermine transfer function that correlates sensor measurements representative of the patient's metabolic need to heart rate, the predetermine transfer function being characterized by a base pacing rate, a maximum pacing rate, and a transition segment defining pacing rates between the base pacing rate and the maximum pacing rate, the method comprising the steps of:

generating pacing pulses at a selectable rate between the base pacing rate and the maximum pacing rate in accordance with the predetermined transfer curve;

sensing the patient's level of metabolic need and generating raw sensor signals representative thereof;

processing the raw sensor signals to derive the sensor measurements;

determining the rate at which pacing pulses are generated based on the sensor measurements and the predetermined transfer function;

processing the sensor measurements to derive first variance measurements, the first variance measurements being based on the difference between a current sensor measurement and at least one previous sensor measurement; and modulating the base pacing rate to a lower pacing rate in accordance with the first variance measurements.

18. The method of claim 17, wherein the step of modulating the base pacing rate comprises modulating the base pacing rate between a prescribed resting rate and a prescribed sleeping rate that is below the resting rate.

19. The method of claim 18, wherein the step of modulating the base pacing rate further comprises setting the base pacing rate to the sleeping rate when a current sensor measurement is below a sensor measurement threshold and a current first variance measurement is below a variance measurement threshold.

20. The method of claim 19, wherein the step of modulating the base pacing rate further comprises setting the base pacing rate to the resting rate when either the current sensor measurement meets or exceeds the sensor measurement threshold, or the current first variance measurement meets or exceeds the variance measurement threshold.

21. The method of claim 19 further comprising the step of maintaining a running average of the sensor measurements, the running average defining the sensor measurement threshold.

22. The method of claim 21, wherein the step of maintaining the running average comprises digitally filtering the sensor measurements using a time constant of about 18 hours.

23. The method of claim 19 further comprising the steps of:

storing first variance measurements derived during a predetermined period of time as a histogram, the histogram including a plurality of bins ranging from a lowest bin to a highest bin, each bin being associated with a different first variance measurement value; and deriving the variance measurement threshold by determining a bin associated with the highest first variance measurement derived while the patient was sleeping.

24. The method of claim 23, wherein the step of deriving the variance measurement threshold comprises:

estimating a number of first variance measurements that were derived while the patient was sleeping during the predetermined period of time in accordance with a prescribed fraction of time that the patient sleeps each day and a total number of first variance measurements stored in the histogram during the predetermined period of time; and counting the first variance measurements stored in the histogram, starting with the lowest bin and proceeding through successively higher bins until the estimated number of first variance measurements that were derived while the patient was sleeping have been counted, the bin associated with the last count defining the highest first variance measurement derived while the patient was sleeping.

25. The method of claim 23, wherein the predetermined period of time is about one week.

26. The method of claim 17, wherein the step of processing the sensor measurements to derive the first variance measurements comprises taking an absolute value of a difference between a current sensor measurement and an earlier sensor measurement, and filtering the result with a recursive, low pass digital filter.

27. The method of claim 26, wherein the current sensor measurement is derived about 26 seconds after the earlier sensor measurement.

28. The method of claim 17, wherein the step of modulating the base pacing rate comprises increasing the base pacing rate from a prescribed sleeping rate that defines a minimum maintained heart rate by an amount defined by the product of a prescribed base rate slope and the first variance measurements.

29. The method of claim 28, wherein:

the step of processing the sensor signals to derive sensor measurements comprises deriving second variance measurements; and the step of applying the sensor measurements to the transfer function comprises the step of applying the second variance measurements to the transition segment of the transfer function to derive the appropriate heart rate for the patient's level of metabolic need.

30. The method of claim 29, wherein the step of applying the second variance measurements to the transition segment comprises increasing the heart rate from the base pacing rate by an amount defined by the product of a prescribed activity slope and the second variance measurements.

31. The method of claim 29, wherein the first variance measurements exhibit less variation over time than the second variance measurements.

32. The method of claim 17, wherein the step of sensing the patient's level of metabolic need comprises sensing levels of physical activity, the levels of physical activity being indicative of the levels of metabolic need.

33. A rate-responsive pacemaker for administering pacing pulses to a patient's heart, comprising:

a pulse generator for generating pacing pulses at a rate between a variable base rate and a maximum pacing rate;

an activity sensor for generating raw sensor signals indicative of the patient's activity level;

control means for determining the rate of pacing pulses generated by the pulse generator, the control means including:
(a) processing means for processing the raw sensor signals to determine activity measurements;
(b) detecting means for detecting when a patient is asleep based on the activity measurements; and
(c) modulating means for varying the base pacing rate between a resting rate and a sleeping rate when the patient is asleep.

34. The pacemaker of claim 33, wherein:

the processing means comprises means for processing the raw sensor measurements to determine activity level measurements and activity variance measurements, the activity variance measurements being based on the difference between a current activity level measurement and at least one earlier activity level measurement; and the detecting means comprises means for detecting when a patient is asleep based on the activity variance measurements.

35. The pacemaker of claim 34, wherein the detecting means further comprises:

threshold determining means for determining an activity variance threshold based on the activity variance measurements, the patient being awake when a current activity variance measurement has a value above the activity variance threshold and asleep when the current activity variance measurement has a value below the activity variance threshold.

36. The pacemaker of claim 35, further comprising:

memory means for storing activity variance measurements derived during a predetermined period of time as a histogram, the histogram including a plurality of bins ranging from a lowest bin to a highest bin, each bin being associated with a different activity variance measurement value, the histogram being bimodal with a dominant mode corresponding to a time period when the patient was sleeping; and wherein the threshold determining means includes means for deriving the activity variance threshold based on a distribution of the dominant mode of the histogram.

37. The pacemaker of claim 35, wherein the modulating means comprises:

means for setting the base pacing rate to the resting rate when either the current activity level measurement meets or exceeds the activity level measurement threshold, or the current activity variance measurement meets or exceeds the activity variance threshold.

38. The pacemaker of claim 35, wherein the modulating means comprises:

means for setting the base pacing rate to the sleeping rate when a current sensor measurement is below the sensor measurement threshold and a current first variance measurement is below the activity variance threshold.

39. The pacemaker of claim 34, further comprising:

memory means for storing a base rate slope; and wherein the modulating means includes means for modulating the base pacing rate by increasing the base pacing rate from the sleeping rate by an amount defined by the product of the base rate slope and the activity variance measurements.

40. A rate-responsive pacemaker for administering pacing pulses to a patient's heart, comprising:

a pulse generator for generating pacing pulses at a rate between a base rate and a maximum pacing rate;

an activity sensor for generating raw sensor signals indicative of the patient's activity level; and control means for determining the rate of pacing pulses generated by the pulse generator, the control means including:

processing means for processing the raw sensor signals to determine activity measurements; and modulating means for continuously adjusting the base pacing rate based on the activity measurements.

* * * * *